(12) United States Patent
Helmlinger

(10) Patent No.: US 7,770,757 B2
(45) Date of Patent: Aug. 10, 2010

(54) MICRODOSING DEVICE FOR A LIQUID MEDIUM

(75) Inventor: Michael Helmlinger, Radolfzell (DE)

(73) Assignee: Ing. Erich Pfeiffer GmbH, Radolfzell (DE)

( * ) Notice: Subject to any disclaimer, the term of this patent is extended or adjusted under 35 U.S.C. 154(b) by 342 days.

(21) Appl. No.: 11/906,047

(22) Filed: Sep. 28, 2007

(65) Prior Publication Data
US 2008/0078783 A1    Apr. 3, 2008

(30) Foreign Application Priority Data
Sep. 29, 2006   (DE) .................. 10 2006 047 658

(51) Int. Cl.
B67D 7/76    (2010.01)
(52) U.S. Cl. .............. 222/189.11; 222/318; 137/115.01
(58) Field of Classification Search .............. 222/196, 222/372, 373, 189.06, 189.08, 189.11, 424; 222/318, 71–73, 1; 239/102.2, 102.1, 4, 239/575, 127, 135; 128/200.14, 200.16; 137/115.01–115.13
See application file for complete search history.

(56) References Cited

U.S. PATENT DOCUMENTS

| | | | |
|---|---|---|---|
| 4,243,059 A * | 1/1981 | Hammon et al. ................ | 137/2 |
| 4,346,727 A * | 8/1982 | Stumpp et al. .......... | 137/115.07 |
| 6,092,691 A * | 7/2000 | Schuerholz et al. ............ | 222/1 |
| 7,584,903 B2 * | 9/2009 | Koerner et al. ........... | 239/102.2 |
| 2004/0031488 A1 * | 2/2004 | Terada et al. ............ | 128/203.15 |
| 2004/0074557 A1 | 4/2004 | Zengerle et al. | |
| 2005/0207917 A1 | 9/2005 | Koerner et al. | |
| 2007/0209659 A1 | 9/2007 | Ivri et al. | |

FOREIGN PATENT DOCUMENTS

| | | |
|---|---|---|
| DE | 101 02 152 C1 | 6/2002 |
| DE | 94 22 442 U1 | 7/2002 |
| DE | 10 2004 006 452 A1 | 8/2005 |
| EP | 0 739 654 A2 | 10/1996 |
| EP | 1 502 606 A1 | 2/2005 |
| GB | 1 575 887 | 10/1980 |
| WO | WO 97/07896 | 3/1997 |

OTHER PUBLICATIONS

European Patent Office Search Report dated Dec. 20, 2007 (5 pages).
Office Action of the Germany Patent Office dated Apr. 17, 2007 (3 pages).

* cited by examiner

*Primary Examiner*—Lien T Ngo
(74) *Attorney, Agent, or Firm*—Flynn, Thiel, Boutell & Tanis, P.C.

(57) ABSTRACT

A microdosing device for a liquid medium includes a dosing compartment and an electrically or electronically activatable vibration unit which can cause at least one contact area of the dosing compartment to vibrate for the delivery of a volume of medium. A medium reservoir is connected to the dosing compartment by at least one flow channel. A manually operable conveyance device for conveying medium to the dosing compartment and/or for conveying medium back from the dosing compartment to the medium reservoir is assigned to the at least one flow channel.

4 Claims, 1 Drawing Sheet

MICRODOSING DEVICE FOR A LIQUID MEDIUM

FIELD OF THE INVENTION

The invention relates to a microdosing device for a liquid medium with a dosing compartment and with an electrically or electronically activatable vibration unit which can cause at least one contact area of the dosing compartment to vibrate for the delivery of a volume of medium and with a medium reservoir which is connected to the dosing compartment by means of at least one flow channel.

BACKGROUND OF THE INVENTION

A microdosing device of this kind is known from DE 10 2004 006 452 A1. In the known microdosing device, the medium volume to be delivered is drawn from a reservoir chamber formed as a capillary and into the dosing compartment by means of corresponding differences in pressure and through capillary action. There is also a filling device which conveys liquid into the reservoir chamber and into the dosing compartment to fill the reservoir chamber and the dosing compartment.

The object of the invention is to create a microdosing device of the type mentioned at the start which is easy to operate and meters out the dose reliably.

SUMMARY OF THE INVENTION

This object is achieved by assigning to the at least one flow channel a manually operable conveyance device for conveying medium to the dosing compartment and/or for conveying medium back from the dosing compartment to the medium reservoir. The solution according to the invention allows an operator to fill the dosing compartment as required and then, when the dosing compartment is completely full, commence delivery. Reliable, uniform dosage is thereby guaranteed. This is advantageous for pharmaceutical and medicinal media in particular, the use of such a device allowing overdosage or underdosage to be avoided. The medium may be conveyed by the conveyance device directly or indirectly. In direct filling, the conveyance device is connected to the dosing compartment via a flow channel. In indirect filling, the conveyance device is used to act on the medium indirectly—through a pressure build-up in particular—in such a way that the medium is conveyed from a medium reservoir to the dosing compartment.

In one embodiment of the invention there is a sensor system which senses a filling operation by the conveyance device and passes on associated signals to a control unit which switches the vibration unit on or off according to the associated signals from the sensor system. This ensures that delivery of the medium in the dosing compartment does not take place until the dosing compartment is completely full. It is not the degree of filling of the dosing compartment which is sensed, but rather the filling operation by the conveyance device. The sensor system advantageously comprises at least one position sensor which senses the starting and/or finishing points of a movement process of the in particular mechanical conveyance device. If filling by the conveyance device is effected indirectly through application of pressure, the application of pressure is sensed. Instead of a position sensor it is also possible to use, in particular, a pressure sensor.

In a further embodiment of the invention, the manually operable conveyance device comprises a mechanical piston pump. The piston pump is operated manually by an operator to produce an appropriate working stroke. A return stroke to the starting position is preferably realized by means of a spring. However, it is also possible, in the mechanical piston pump, to merely initiate the stroke process manually and effect the subsequent working stroke by means of a spring, using a pretensioned spring unit. A further spring unit can then be responsible for the return stroke. In this way, uniform filling of the dosing compartment is always achieved, irrespective of the user.

If a preposed dosing chamber, formed in particular as a capillary, is additionally assigned to the dosing compartment, it is advantageous if the volume conveyed by the manually operable mechanical conveyance device is such that both the dosing compartment and the preposed dosing chamber can be filled by a single working stroke.

In a further embodiment of the invention, at least one flow channel between the dosing compartment and the medium reservoir and/or between the dosing compartment and the conveyance device and/or between the conveyance device and the medium reservoir has at least one valve arrangement. This ensures that incorrect flows of the medium are avoided. In particular, it means that it is possible to prevent contaminated medium which has already come into contact with environmental air in the dosing compartment region from becoming mixed with as yet uncontaminated medium from the medium reservoir.

In a further embodiment of the invention, the valve arrangement opens or closes according to the pressure. In a further embodiment, the valve arrangement is a mechanical nonreturn valve. This prevents medium from flowing back or being drawn back against the desired direction of flow, which would be undesirable.

In a further embodiment of the invention, the flow channel between the medium reservoir and the dosing compartment has a filter device, in particular a microbial filter device. This ensures that no contaminated medium can pass into the medium reservoir via the flow channel. The medium in the medium reservoir itself, preferably a suitable pharmaceutical liquid, is microbiologically pure. The medium reservoir is sealed, such that no environmental gases can enter the medium reservoir.

BRIEF DESCRIPTION OF THE DRAWINGS

Further advantages and features of the invention are specified in the claims and in the following description of preferred embodiment examples of the invention, which are presented with the aid of the drawings.

DETAILED DESCRIPTION

Figure 1:
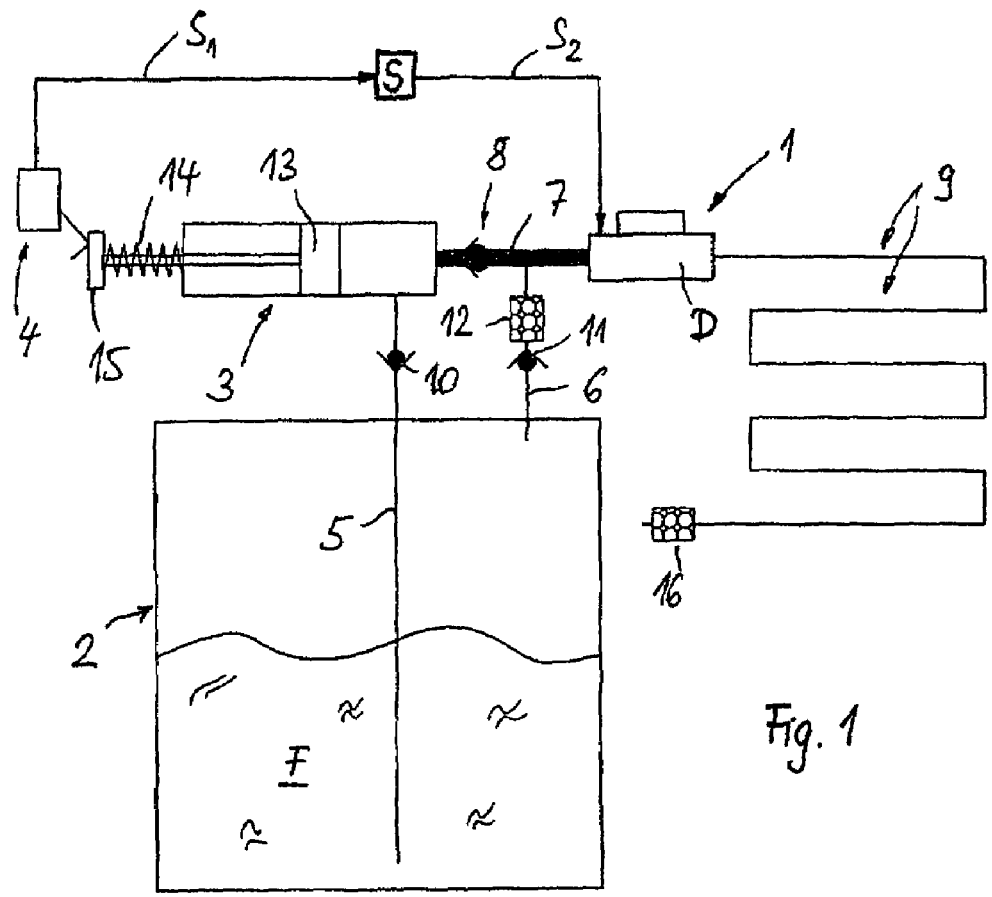
FIG. 1 shows a schematic diagram of an embodiment of a microdosing device according to the invention, in which direct filling of a dosing compartment is effected by means of a mechanical conveyance device

A microdosing device according to FIG. 1 is used to deliver liquid media in small quantities and with highly precise dosing. Such a microdosing device is envisaged as particularly advantageous for medical indications, for delivering pharmaceutical liquids. However, the microdosing device may equally be used for other purposes too. For highly precise dosing, the microdosing device has a dosing compartment D which on one side is open to the environment through numerous microscopically small delivery apertures and which on a side located away from the delivery side has a contact area with a vibration unit assigned to it. The vibration unit is preferably formed as a piezo element and capable of being caused to vibrate, by electrical or electronic means of control, such that the contact area of the dosing compartment vibrates. These vibrations, through the corresponding capillary forces, cause the liquid medium in the dosing compartment to pass through the microscopically small delivery apertures and out into the environment. Attached to the dosing compartment D—which is also known as the dosing chamber—and communicating with it is a preposed dosing chamber 9 which is formed as a capillary. The preposed dosing chamber 9 end that faces away from the dosing compartment D is open. The open area has a microbial filter unit 16 to allow pressure equalization with the environment but also to prevent contaminated air from being able to penetrate the preposed dosing chamber 9.

The basic structure of the delivery unit formed by the vibration unit, the dosing compartment D, the delivery apertures, and the preposed dosing chamber corresponds to the constructional unit known from DE 10 2004 006 452 A1, so reference should also be made to the contents of that document for further details.

To enable the dosing compartment D and the preposed dosing chamber 9 to be filled, the dosing compartment D, on a side facing away from the preposed dosing chamber 9, is connected to a flow channel 7, which is connected to a medium reservoir 2 via an offbranching backflow channel 6, which is likewise a flow channel. The flow cross-section of the flow channel 7 is many times greater than the flow cross-section of the backflow channel 6.

The medium reservoir 2 stores a liquid F that serves as a medium, in a hermetically sealed state. Projecting into the medium reservoir 2 is a flow channel 5 which serves as a suction channel and whose open inlet port lies below the surface of the liquid F and is thus permanently immersed in the liquid F as long as the medium reservoir 2 is not essentially empty. The suction channel 5 is connected to a conveyance device 3 which serves as a filling device and which is formed as a manually operable thrust piston pump. The conveyance device 3 has a working piston 13 which can be moved linearly in a corresponding working cylinder. Through movement of the working piston, the volume of a cylinder space of the working cylinder is modified in a basically known manner. Connected to the cylinder space of the working cylinder is the flow channel 7, which leads to the dosing compartment D. The cylinder space is also connected to the suction channel 5, which opens into the medium reservoir 2. A piston rod of the working piston 13 projects from the working cylinder and, at its external, anterior end, has a stop block 15, which supports a return spring arrangement 14. The return spring arrangement 14 serves to return the working piston 13 to a starting position after a corresponding operating stroke.

To detect a movement of the working piston 13 away from its starting position as shown in FIG. 1 or back to the starting position, a sensor system 4 in the form of a limit switch which is connected to an electrical or electronic control unit S via a signal lead $S_1$ is assigned to the stop block 15. The control unit S controls the activation or the deactivation of the vibration unit via a control lead $S_2$.

Assigned to the suction channel 5 is a nonreturn valve 10 which opens in the direction of the cylinder space and which prevents liquid that is already in the cylinder space of the conveyance device 3 from being able to flow back into the medium reservoir 2. A nonreturn valve 8 which opens in the direction of the dosing compartment D to prevent liquid from the flow channel 7 and from the dosing compartment D from being able to flow back into the cylinder space of the conveyance device 3 is also assigned to the flow channel 7. Finally, the backflow channel 6 too is provided with a nonreturn valve 11 that opens in the direction of the medium reservoir 2. The nonreturn valve 11 serves to close the backflow channel 6 as soon as the pressure in the medium reservoir 2 is greater than that in the flow channel 7. Connected upstream of the nonreturn valve 11 is a filter device 12, which is thus sited on the backflow channel 6 between the flow channel 7 and the nonreturn valve 11. The filter device 12 is a microbial filter. This prevents contaminated liquid from the dosing compartment D and from the flow channel 7 from being able to flow back into the medium reservoir 2. The contaminants are retained in the filter device 12.

The described arrangement ensures that the liquid F in the medium reservoir 2 remains clean and thus uncontaminated.

OPERATION

The microdosing device shown in FIG. 1 works as follows:

To fill the dosing compartment D and the preposed dosing chamber 9 with liquid F, liquid F is first drawn into the cylinder space of the conveyance device 3 via the suction channel 5 through the execution of a corresponding stroke by the working piston 13. This initial filling of the cylinder space can be described as priming. Appropriately, no control action is effected in regard to the vibration unit during this initial filling even though the operating stroke in question is duly detected by the limit switch of the sensor system 4. As soon as the cylinder space has been filled, the dosing compartment D and the preposed dosing chamber 9 can be filled in a next stroke or in several strokes. For this, the working piston 13 is pressed manually in the direction of the flow channel 7, as a result of which the corresponding flow pressure opens the nonreturn valve 8 and the liquid flows into the dosing compartment D and the preposed dosing chamber 9. It is preferable if a working stroke of the working piston 13, and thus the volume of the cylinder space, is matched to the filling volume of the dosing compartment D and the preposed dosing chamber 9 such that the dosing compartment D and the preposed dosing chamber 9 are adequately filled by a single stroke of the working piston 13. As a result of the pressure build-up within the cylinder space, the nonreturn valve 10 of the suction channel 5 is automatically closed, so no liquid can be forced back into the medium reservoir 2. Furthermore, since the flow cross-sections of the flow channel 7 and the backflow channel 6 are very different as mentioned above, the flow resistance within the backflow channel 6 is so great that the liquid is forced into the dosing compartment D without any side stream being diverted into the backflow channel 6.

On a corresponding return stroke of the working piston 13, liquid F is automatically drawn into the cylinder space once more. On the corresponding return stroke, which, following the removal of the manually applied pressure, is effected by the elastic force of the return spring arrangement 14, the nonreturn valve 8 of the flow channel 7 is closed, which means that liquid now cannot be drawn back from the dosing compartment D or from the flow channel 7. After the described strokes of the working piston 13, the dosing compartment D and the preposed dosing chamber 9, and also the cylinder space of the conveyance device 3, are now full. As soon as a further working stroke of the working piston 13 is manually initiated, the vibration unit is activated through the control unit S at the same time as the piston movement is initiated, resulting in a delivery action. As soon as the stop block 15 strikes the limit switch again in a subsequent return stroke of the working piston 13, the vibration unit can be deactivated.

However, it is also possible to have the control unit S effect other control actions in respect of the vibration unit, on the basis of appropriate signals from the sensor system. If the control unit S has intelligent electronics, different control programs can be programmed in, and executed, accordingly. In particular, excess liquid in the flow channel 7 can flow away into the medium reservoir 2 through the backflow channel 6. If the medium reservoir 2 is formed as a closed pressure vessel, the removal of liquid F from the medium reservoir 2 necessarily produces a negative pressure which can generate a corresponding suction pressure to open the nonreturn valve 11 of the backflow channel 6 and thus draw excess liquid from the flow channel 7 and from the dosing compartment D and preposed dosing chamber 9 back into the medium reservoir 2. This is particularly advantageous in cases where, in a corresponding delivery action by the vibration unit, the dosing compartment D and/or the preposed dosing chamber are not completely emptied.

Figure 2:
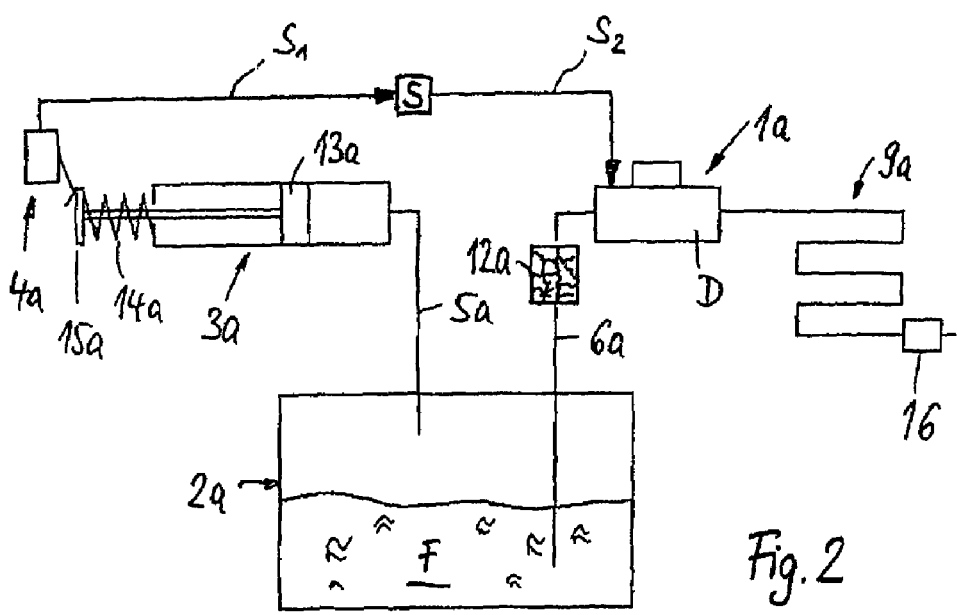
FIG. 2 shows another embodiment of a microdosing device according to the invention, in which indirect filling of the dosing compartment is effected by applying pressure to a medium reservoir.

In terms of basic structure, the microdosing device as shown in FIG. 2 corresponds to the microdosing device shown in FIG. 1, so reference should also be made to the disclosure of the embodiment shown in FIG. 1. Constructional units and parts with the same function are given the same reference numbers as in the embodiment shown in FIG. 1, but with the addition of the letter a. A fundamental difference of the embodiment shown in FIG. 2 is that the dosing compartment D and the preposed dosing chamber 9a are not filled directly by the conveyance device 3a; instead, filling is effected indirectly by applying appropriate pressure to the pressure-tight medium reservoir 2a. For this, there is a flow channel 6a which connects the medium reservoir 2a to the dosing compartment D and which is formed as a suction channel for the liquid F. The suction channel 6a projects into the liquid F in a similar manner to the suction channel 5 in FIG. 1. The conveyance device 3a, on the other hand, is only connected to the medium reservoir 2a by a pressure channel 5a in the manner of a pressure vessel, by the pressure channel 5a in question merely projecting into the top part of the medium reservoir 2a without necessarily coming into contact with the liquid F.

The application of pressure, preferably manual pressure, to the piston 13a results in a linear piston movement which reduces the cylinder space and places the medium reservoir 2a under pressure via the pressure channel 5a.

A corresponding pressure build-up in the medium reservoir 2a leads to a positive pressure in the medium reservoir, thereby forcing the liquid F through the flow channel 6a and into the dosing compartment D and the preposed dosing chamber 9a. Activation, preferably simultaneous activation, of the vibration unit to deliver the liquid in the dosing compartment D produces the desired emptying of the dosing compartment D and, where applicable, of the preposed dosing chamber 9a. The pressure conditions should also be advantageously organized, such that there is no permanent discharging of liquid in the area of the delivery apertures of the dosing compartment D.

During the delivery of medium from the dosing compartment D to the environment, the piston 13a must be kept depressed, against the elastic force of the return spring 14a. The control unit S is advantageously arranged so that the vibration unit remains activated during the application of pressure by the piston 13a. As soon as the pressure applied to the piston 13a is removed, preferably through the removal of the manually applied pressure, the return spring 14a returns the piston to the nonloaded starting position shown in FIG. 2. Because of the intercommunicating spaces, namely the cylinder space and the space in the medium reservoir 2a, this gives rise to a negative pressure in the medium reservoir 2a, causing medium residues left over in the dosing compartment D to be drawn back. To prevent contaminants in the dosing compartment from reaching the medium reservoir, a filter unit 12a, which is preferably effective against microbes, is provided. This retains contaminants, so the liquid in the medium reservoir remains clean. The return of the piston 13a to the starting position elicits a sensor signal from the sensor unit 4a, allowing the vibration unit to be switched off via the control unit S.

The invention claimed is:

1. Microdosing device for a liquid medium comprising a dosing compartment and an electrically or electronically activatable vibration unit which can cause at least one contact area of the dosing compartment to vibrate for the delivery of a volume of medium and a medium reservoir which is connected to the dosing compartment by means of a first flow channel,
    wherein a manually operable mechanical piston pump for conveying medium to the dosing compartment is assigned to said first flow channel,
    wherein said first flow channel comprises a mechanical nonreturn valve between said piston pump and the dosing compartment, said nonreturn valve inhibiting back flow of contaminated liquid medium from the dosing compartment to the piston pump, and
    wherein a second flow channel branches off from said first flow channel between the nonreturn valve and the dosing compartment to the medium reservoir, said second flow channel having a filter device.

2. Microdosing device according to claim 1, wherein the mechanical piston pump includes a sensor system and a control unit, the sensor system sensing a filling operation by the mechanical piston pump and passes on associated signals to the control unit which switches the vibration unit on or off according to associated signals from the sensor system.

3. Microdosing device according to claim 1, wherein a flow cross-section of the first flow channel is many times greater than a flow cross-section of the second flow channel.

4. Microdosing device according to claim 1, wherein the second flow channel also includes a further nonreturn valve connected in series with the filter device for inhibiting back flow of medium in the medium reservoir to the first flow channel.

* * * * *